(12) United States Patent
Tubbs

(10) Patent No.: US 6,629,942 B1
(45) Date of Patent: Oct. 7, 2003

(54) DEVICES AND METHODS FOR ABDOMINAL SUPPORT

(76) Inventor: J. C. Tubbs, 10655 Morning Ridge Dr., Moreno Valley, CA (US) 92557-4200

( * ) Notice: Subject to any disclaimer, the term of this patent is extended or adjusted under 35 U.S.C. 154(b) by 0 days.

(21) Appl. No.: 09/353,858

(22) Filed: Jul. 15, 1999

(51) Int. Cl.$^7$ ................................................ A61F 5/00
(52) U.S. Cl. ........................................... 602/13; 602/19
(58) Field of Search .............................. 128/846, 888, 128/889, 869, 876; 602/13, 19

(56) References Cited

U.S. PATENT DOCUMENTS

| | | | | |
|---|---|---|---|---|
| 2,663,020 A | * | 12/1953 | Cushman | 128/888 |
| 3,026,874 A | * | 3/1962 | Stevens | 128/888 |
| 3,521,623 A | * | 7/1970 | Nichols | 602/13 |
| 4,120,297 A | | 10/1978 | Rabischong et al. | |
| 4,438,763 A | | 3/1984 | Zablen | |
| 5,111,807 A | * | 5/1992 | Spahn et al. | 602/13 |
| 5,257,419 A | | 11/1993 | Alexander | |
| 5,437,615 A | * | 8/1995 | Pekar et al. | 602/13 |
| 5,769,800 A | | 6/1998 | Gelfand et al. | |

* cited by examiner

Primary Examiner—Michael A. Brown
(74) Attorney, Agent, or Firm—Law Offices of Uleses C. Henderson, Jr.

(57) ABSTRACT

A mechanism for supporting and relieving pain of an abdominal incision comprises a radially expandable bladder, a rigid waist band and a partial body garment. The expandable bladder comprises a pad, which spans a substantial portion of the abdominal region, is pressurized to apply pressure forces to the abdomen. The encircling and inelastic band overlays the entire inflatable bag and is adjustably closable at the back of the patient by fastener means. In an initial recovery period after the surgical procedure, the radially expandable bladder and the encircling band are both encompassed within a flexible body garment which can encircle at least upper-thigh region, and which compresses all zones above, below and on the sides of the incision zone, limiting the forces in the plane of the tissues that tend to act upon the incision zone, but without interfering with or impeding body movements. Thus, in the initial period after surgery, the patient can sleep and engage in permissible movements with less discomfort, and less danger of disruption of the sutures, while accelerating recovery. At a later interval, the bladder and encircling band need not be employed, and the patient can use only the partial or full body suit.

21 Claims, 10 Drawing Sheets

DEVICES AND METHODS FOR ABDOMINAL SUPPORT

FIELD OF THE INVENTION

This invention relates to safeguarding against damage to weakened abdominal areas, and more particularly to devices and methods for relieving pain and promoting healing after invasive abdominal surgery and promoting healing.

BACKGROUND OF THE INVENTION

After surgery in the abdominal region of a patient, the patient is exposed to dangers and subjected to discomfort that is not encountered when surgery is conducted in other regions of the body. In a sense, physical activity of the trunk of the body or of the limbs cannot be conducted without affecting the muscle and tissue in the abdominal region, since even though it is not actively involved in work or exercise activities, it is passively affected by forces acting from all sides. Even when asleep, a person's motions can affect the central abdominal region, which by its geometry cannot readily be bound up or confined against motion without extreme discomfort to the patient.

If an incision is made in the abdominal region for surgical procedures, for example, the incision is closed and sutured at the end of the procedure, and the patient must thereafter protect the sutured zone against forces which would strain the sutures and/or tend to reopen the wound, while also undergoing the pain that accompanies an incision in this sensitive region. The acute phase of the healing process takes a few hours to several days, as the incision space first fills with serum and blood and then neutrophilic infiltration of the dermis takes place. At this point the edges of the incision which are held in place have little resistance to tensile forces except that provided by the suture. This condition gradually changes as neutrophilic activity first increases and then is supplanted by macrophage activity and subsequently by the formulation of granulation tissue and then neovascularization and collagen fiber formation. This leads to increasing tensile strength as the granulation tissue transforms into a collagen filled scar.

Thus care may have to be exercised for a considerable time because of the slowness and gradual changes in the healing procedure. However, although there are a number of abdominal supports that are known, typically in the form of elastic garments covering the body and the waist to thigh region, there are no accepted expedients of this character which aid in reducing pain, promote healing and provide protection against reopening of the incision.

The known elastic garments function essentially to compress all of the lower body region, thus typically limiting tissue movement from the zone of the incision in different directions instigated by bodily movements. A person having substantial adipose tissue in this region cannot control forces that impel motion in the incision zone because of body movement elsewhere, which may not only induce pain but actually contribute to separation of the joined tissue walls at the incision. A close fitting elastic garment that covers the entire region can have some beneficial restraining effect, but actually in most instances, depending on body structure, this tends to increase, rather than alleviate the discomfort. Straps and belts are also used in different configurations and while they can be even more restrictive on tissue displacement they have less local benefit in the zone of the incision and tend to inhibit bodily freedom.

SUMMARY OF THE INVENTION

Devices and methods in accordance with the invention provide at least two different pressure exerting constraints in the regions proximate to and surrounding the incision zone. One constraint is provided by an expandable element of limited area in contact with the incision and the area immediately around it. The expandable element is expanded to a comfortable pressure level by an interior compressible fluid. The expandable element is confined within another element, which encircles the body and is inelastic, but conformable to the body configuration. By locally exerting distributed forces on the abdominal surface at and about the incision zone, the tissues in that zone are restricted from drastic movement, and the facing walls of the incision are forced together while at the same time, the pressure on the incision reduces pain and irritation. Concurrently, the compressible fluid, such as gas, allows local yielding to forces and movements in the proximal zone. Both the gas pressure and encircling band can be adjusted for comfort and pain relief. In an initial recovery period after the surgical procedure, the radially expandable element or bladder, and the encircling band are both encompassed within a flexible body garment which can encompass at least the upper-thigh region, so as to lightly compress all zones above, below and on the sides of the incision zone, limiting the forces in the plane of the tissues that tend to act upon the incision zone, but without interfering with or impeding body movements. Thus, in the initial period after surgery, the patient can sleep and engage in natural involuntary movements with less discomfort, and less danger of disruption of the sutures, while accelerating recovery. At later stages, as healing progresses, either the body garment or the bladder and encircling band need not be employed.

In a more particular example of a device in accordance with the invention, the radially expandable bladder comprises a pad which spans a substantial portion of the side of the abdomen as well as the major part of the frontal portion of the abdomen, while the encircling and elastic band overlays the entire expandable bladder and is adjustably closable at the back of the patient by fastener means such as buckles, Velcro or other known methods. This structure is adjustable for size, shape and comfort and readily reusable.

A number of alternatives in accordance with the invention are also feasible, including an encircling band or belt which has an aperture in the abdominal region which is smaller in area than the expandable bladder, thus holding the bladder about its periphery against the body but modifying the forces acting on the incision zone, because the bladder can be pumped to a higher pressure, since it is free to expand outwardly. As another alternative, the expandable bladder, a pump for generating pressure in the bladder and the encircling waistband can be made as a single integral unit. In addition, an optional elastic body garment can be of different sizes, but nonadjustable except for its inherent elasticity, or made in one size and provided with adjustable enclosures.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
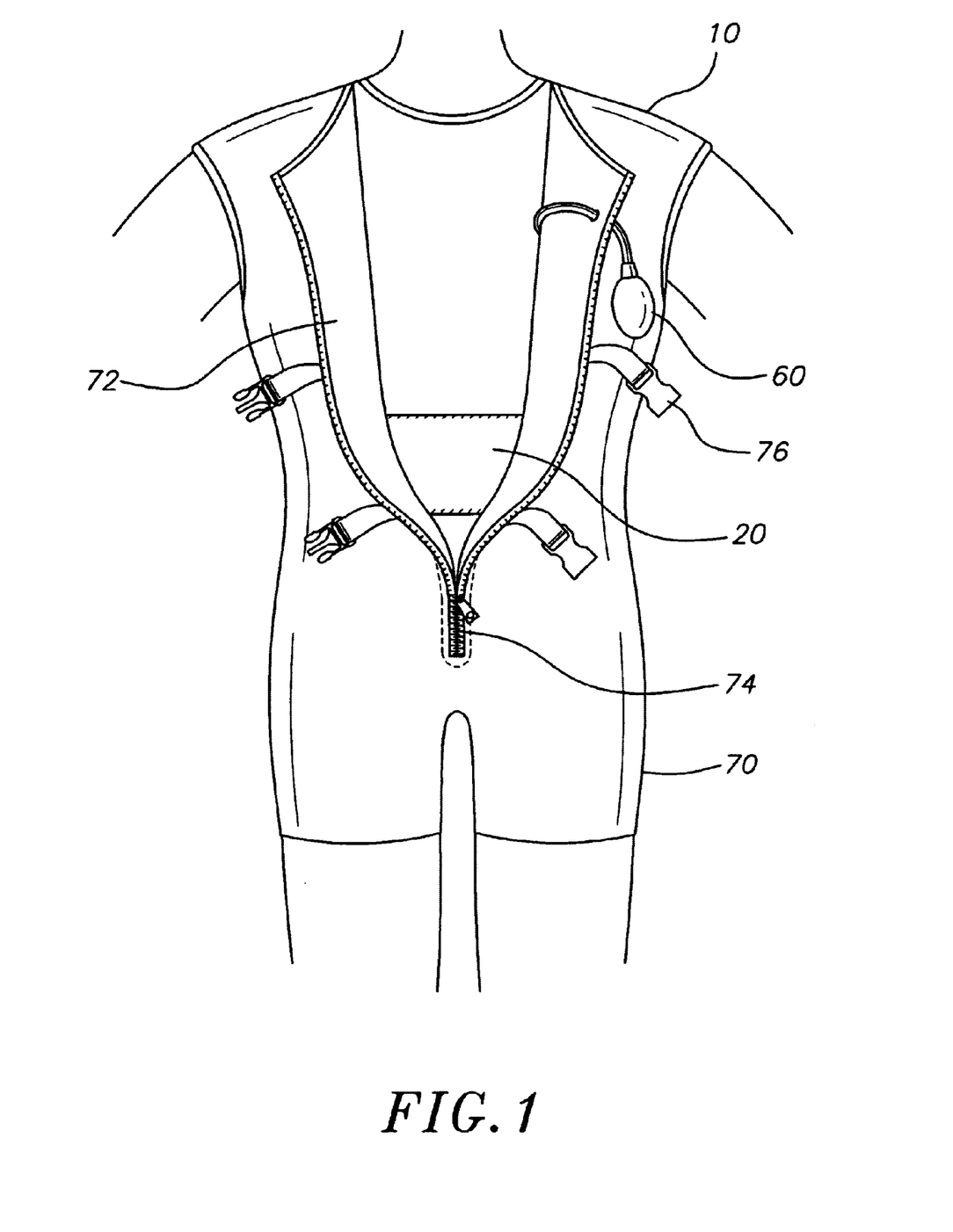
FIG. 1 is a front view of a preferred embodiment of the abdominal support mechanism.

Most abdominal incision are made in the central region of the lower torso. These incisions are generally a few inches in length, spanning a length, along the central portion of the abdomen. Once the surgery has been completed, the incision is closed, typically by a suture. Healing of the incision involves a critical period of several days that is most critical at the outset, with tissue integrity being restored over the course of a few weeks. During the initial period it is very important for the incision not to be subjected to sudden movements which might strain the suture or otherwise cause the incision walls to tear or reopen. It is therefore important to provide support at the incision area in order to restrain any unnecessary abdominal movement, but to do so in a manner which itself is not uncomfortable. Applying a sufficient amount of pressure to a sutured area has been found to alleviate abdominal pain, as the pressure both desensitizes and provides a feeling of security. The present invention provides a mechanism and method of providing abdominal support that enhances healing of post surgical incisions that are typically closed by sutures, although other means are now available for use. FIG. 1 depicts an abdominal support system comprising a restraining band 20 and a compression suit 70, which overlies the band 20 and the trunk of the body.

Figure 2:
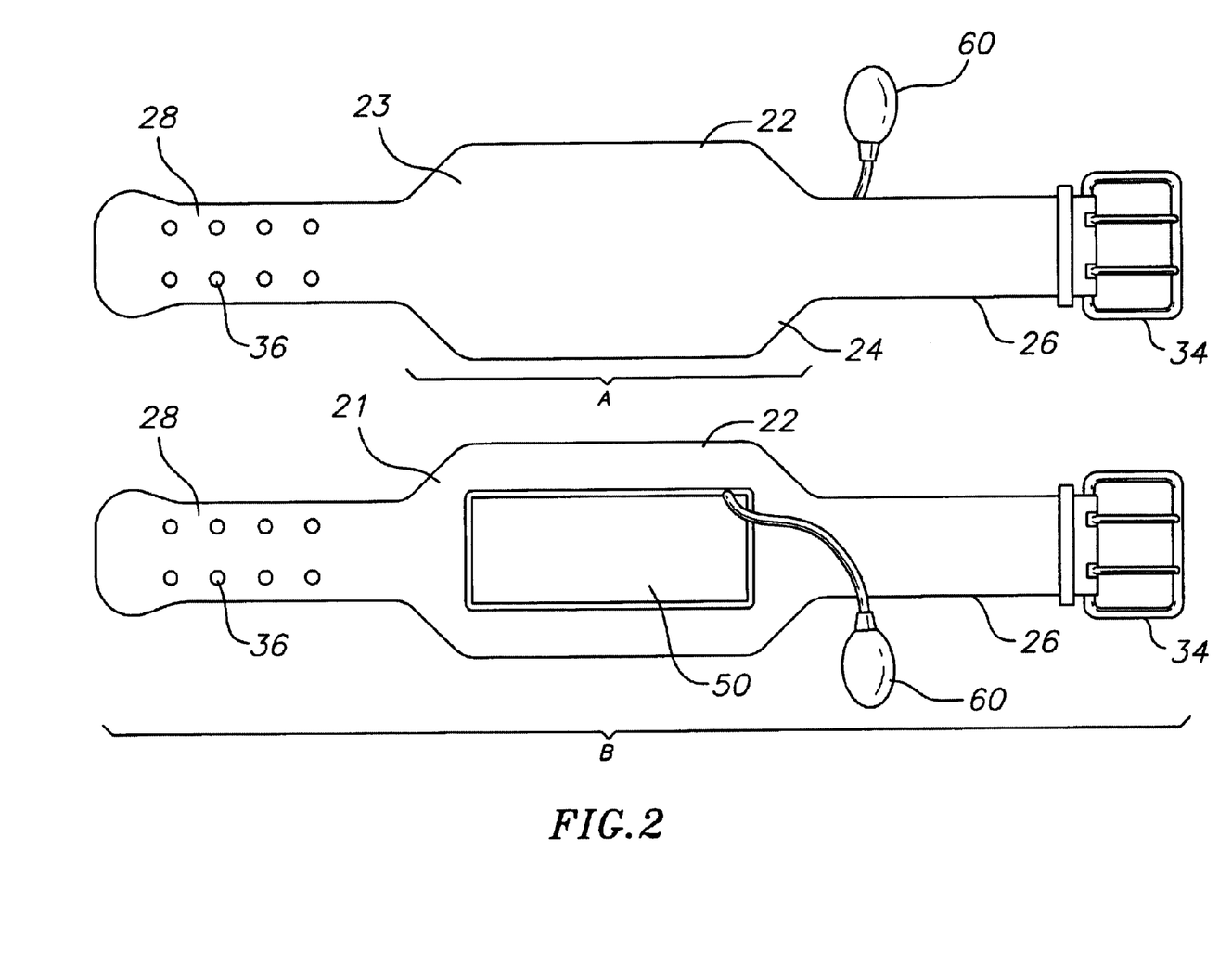
FIG. 2 is a plan view of a restraining band in accordance with the invention.

In preferred embodiments, as shown in FIG. 2, the restraining band 20 is designed to adjustably fit around a patient's waist. The restraining band 20 comprises a band 22, for fitting about the waist of the user, and a radially expandable bladder 50 within the band for engagement against the incision in the abdomen. Once the restraining band is secured around the patient's waist, the bladder 50 can be inflated in a controlled manner to apply radial circumferential pressure to the abdomen.

The waist band 22 is preferably made from a pliant material, such as a tightly woven canvas, and is designed to be fastened around the patient's waist for holding the interior bladder 50 against the abdomen. The waist band 22 comprises an elongated, substantially flat central band 24 having an inner surface 21, an outer surface 23 and length A. The central band 24 is coupled to a first strap end 26 and a second strap end 28. The waist band 22 is tapered such that its width is approximately 13 inches in the center of the central band 24 and approximately 11 inches at both ends 26 and 28. The total length B of the waist band 22, which includes the length of the central band 24 and the first strap end 26 and second strap end 28, is preferably slightly greater than that of the waist of the patient so the strap ends 26 and 28 may be overlapped to encircle the waist. For example, for a waist of about 36 inches, the length of A is preferably about 24 inches and each of the strap ends 26 and 28 are about 8 inches such that the total length B of the waist band 22 is about 40 inches.

In alternative embodiments, the waist band 22 may comprise other materials, such as, but not limited to, hard rubber, leather and other materials exhibiting similar material properties. Additionally, the dimension of the waist band 22 will vary according to dimension of the user.

The first strap end 26 includes an attached fastener 34, such as a buckle. The second strap end 28 comprises a series of holes 36 displaced along its length for receiving the fastener 34. The first strap end 26 acts in conjunction with the second strap end 28 to secure the waist band 22 around the patient's waist and enables the waist band 22 to be adjustable. In alternative embodiments, other adjustable fastening methods made be used to secure the waist band 22, including, but not limited to, Velcro fabrics and adjustable snap locks.

Figure 3:
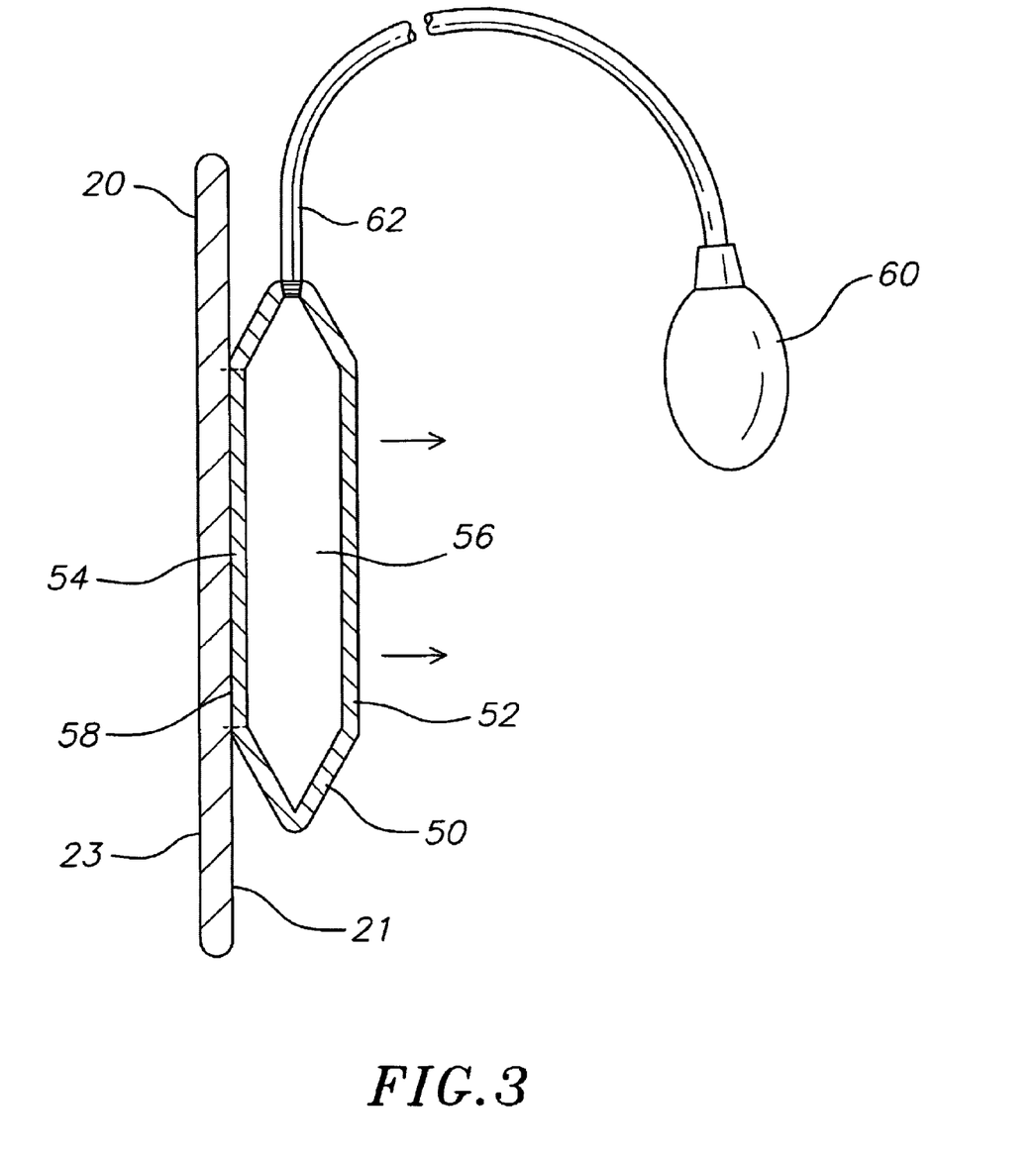
FIG. 3 is a sectional view of the restraining band in FIG. 2. in accordance with the invention.

With reference to FIG. 3, the expandable bladder 50 is designed to substantially encircle the abdominal area and may extend about the sides and a portion of the lower back. The expandable bladder 50 is pressurizable with gas to apply a constant pressure distributed across the patient's abdomen regardless of how tight the waist band 22 is initially applied. The bladder 50 is made of an impermeable material, such as a nylon fabric coated with polyurethane, and comprises an inner wall 52 and an outer wall 54, each having surface dimensions 11 inches by 20 inches. The walls 52 and 54 thus define an enclosed volume 56, which can be filled with a compressible fluid, such as air. The bladder 50 is fastened to the inner surface 21 in the middle of the central band 24 at a seam 58. This design geometry allows the bladder 50 to expand radially, relative to the body, when inflated. Radial expansion is achieved by the use of an inextensible material, having no significant ballooning when inflated, and the circumferential inelasticity of the supporting central band 24, which permits extension of the bladder 50 only in one direction. When the bladder 50 is inflated it expands radially, contacting the abdominal area and conforming to the patient's contour. Once in contact with the abdomen, the bladder 50 can be further pressurized to apply a consistent circumferential compression to the suture. Both the bladder 50 and the waist band 22 can be individually adjusted for fit, comfort, and alleviation of pain.

The expandable bladder 50 may comprise other materials, including, but not limited to, plastic, nylon, silicone and latex. The dimensions of the expandable bladder 50 are to vary in proportion to the dimensions of the waist band 22 and the user.

A hand pump 60 is used to control the pressurization of the bladder 50. The pump 60 is attached to the bladder 50, via a pressure line 62, pressurizing the bladder 50 with a compressible fluid. The hand pump 60 includes a pressure release valve such that the bladder 50 may be inflated or deflated to achieve a comfortable circumferential pressure on the abdomen.

The compression suit 70, as presented in FIG. 1, is made of a flexible material, such as a light canvas, and encircles the patient's whole torso and upper-thigh region. The compression suit 70 includes an inner liner 72, a fastening seam 74 and a pair of adjustable secondary fasteners 76. The compression suit is designed to fit over the retaining belt 20 with the inner liner 72 compressing against outer surfaces of the retaining band 20. The suit 70 additionally provides secondary compressive pressure to the upper torso and upper thigh areas that surround and support the abdominal area as well.

The fastening seam 74, such as a zipper, extends along the frontal area of the suit to enable the user to dress or remove the suit 70, as well as providing a means for initializing the suit's 70 compressive forces on the body. A pair of secondary fasteners 76, such as snap locks, are located on the frontal area of the body suit, and configured, perpendicular to the fastening seam 74, to provide additional compression means for the suit 70 and enabling the suit to taper with the body.

In alternative embodiments, the suit 70 may be made of other materials, such as nylon, rubber, neoprene, or elastic foam composites. Other fastening means may be used along the seam 74, including Velcro, in addition to locating the seam 74 in alternative configurations, such as along the side of the suit 70 or along it's back. Additionally, other secondary fastening means may be used to taper the suit 70, including, but limited to, an adjustable belt loop and Velcro straps.

Figure 4:
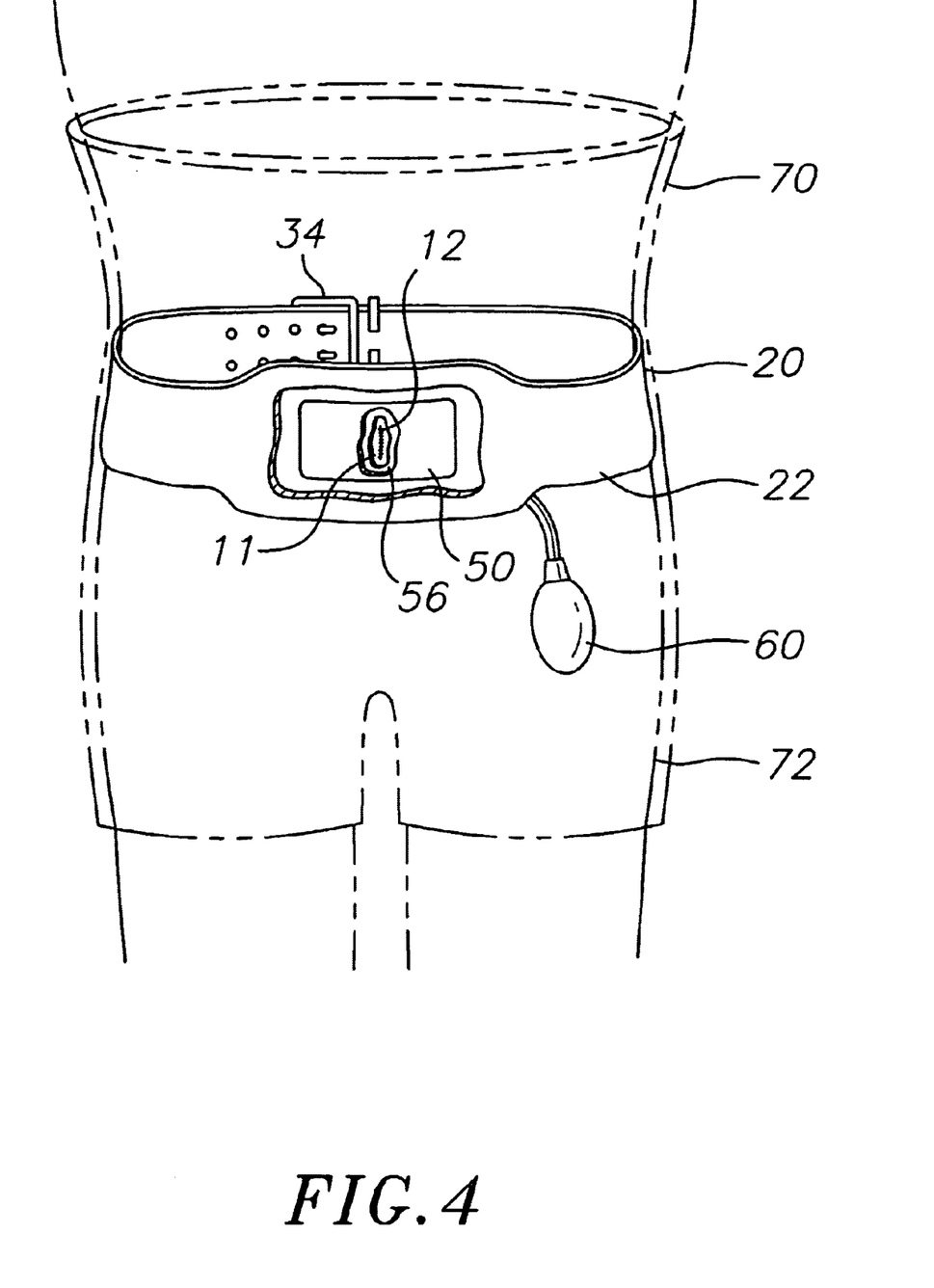
FIG. 4 is a perspective view of the principal elements of the abdominal support mechanism in FIG. 1 while in use, and showing further details thereof.
Figure 5:
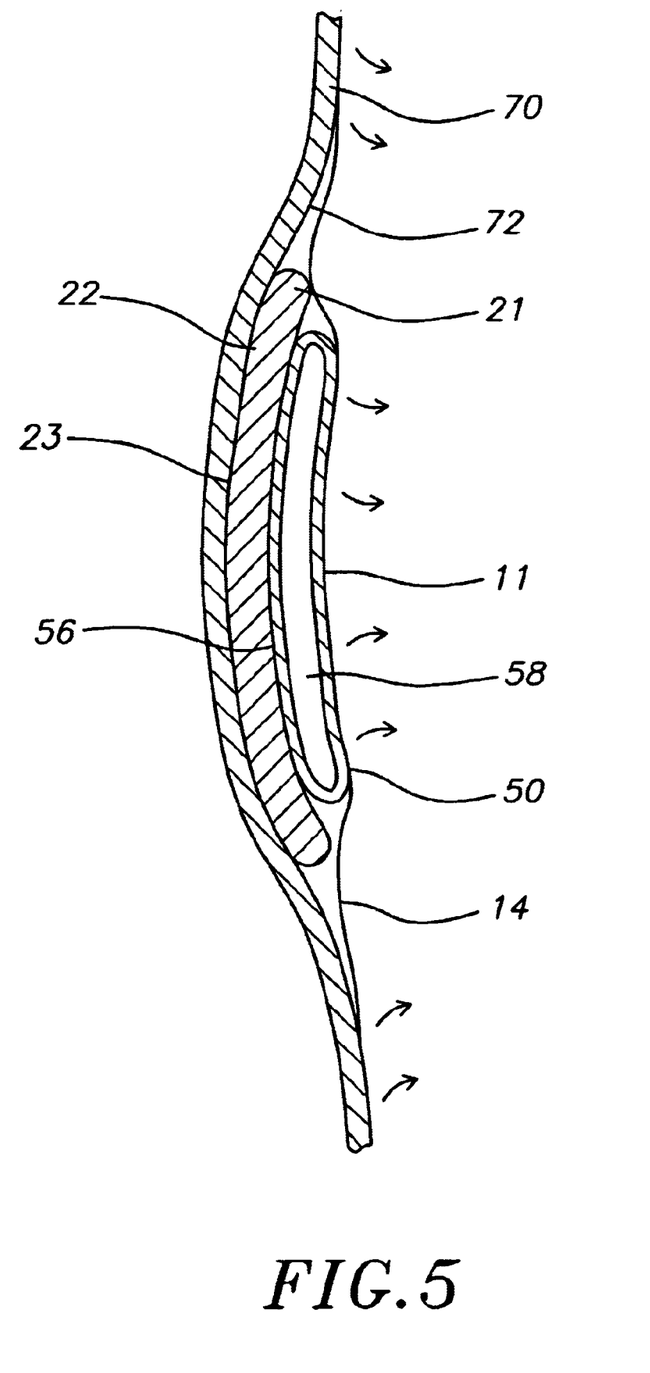
FIG. 5 is a fragmentary cross-sectional view of a preferred embodiment of the abdominal support mechanism in support of the frontal abdominal area in accordance with the invention.

In usage, as seen in FIGS. 4 and 5, the restraining band 20 is wrapped circumferentially around the waist of the patient after surgery. Assistance of a medical technician may be required to provide proper fitting and comfort. The restraining belt 20 can be adjusted to provide adequate restraint about the abdominal area. Once the restraining belt 20 is secured in place, the inflatable bladder 50 is then pressurized to a sufficient pressure to support the crucial abdominal area 12 containing the incision 11. Once pressurized, the restraining belt 20 conforms to the dimensions of the user and exerts localized pressure forces perpindicularly on the incision 11 and the proximal area 12. The localized pressure forces are determined by interior forces of the compressible gas and the exterior circumferential tension created by the restraining belt 20. These are set to provide distributed pressure loads in the abdominal area, which act to restrain the sutured wall tissues at the incision, and the tissues encompassing the incisions, from lateral movement relative to the incision and at the same time, pressing in on the incision 12. The hoop stresses created by the restraining band 20 act to bring all the compressive forces to a focal pressure point within the abdomen. The pressure acts to force the facing walls of the incision 12 together, facilitating the healing process and further, reducing pain and irritation. Because the bladder 50 is pressurized with a compressible fluid, it yields to the counter forces from the body side that are adequate to overcome the constraint. This means the user does not feel extra resistance to movement, even though the incision is securely held. The dual function of the bladder 50 and belt 22 provides the pressure to restrain the incision 12 separation or tearing. The restraining belt 20 is designed to be worn consistently throughout the healing process.

During the first few weeks after surgery, the compression suit 70 is preferably worn in tandem with the restraining band 20 during the patent's sleeping hours. The compression suit 70 acts to provide secondary support and pressure to abdominal area, restricting unconscious bodily motions which might cause the incision 12 to open or tear while sleeping. The suit 70 also acts to restrict motion in areas surrounding the abdomen to relieve any additional stress which might be transferred from the trunk of any adjacent limbs to the abdomen. The adjustable fasteners 76 provide additional comfort and taper.

Figure 6:
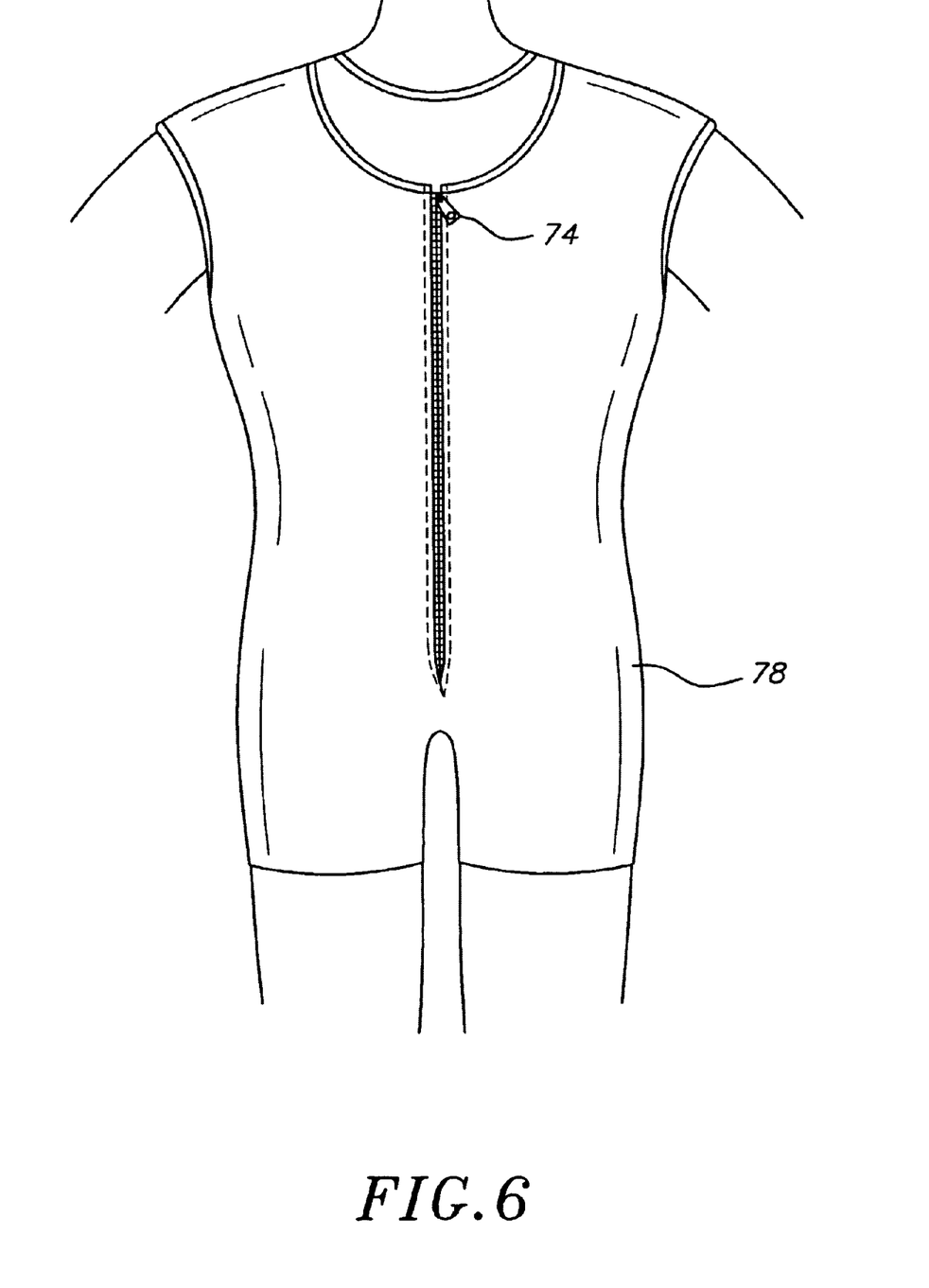
FIG. 6 is a front view of a casual support suit in accordance with the invention.

After about three weeks, a casual suit 78 may be worn alone during waking hours, as shown in FIG. 6. The suit 78 comprises an elastic material, such as neoprene, and encircles the patient's whole torso and upper-thigh region. The suit 78 having compressive material properties, provides adequate support to the abdomen and surrounding areas, as progressive healing of the incision 12 now requires less pressure to provide relieve. After about 5 weeks, the incision will likely have had adequate time to heal. Use of the body suit is recommended as needed.

In alternative embodiments, the casual suit 78, may be replaced by a compliant full body suit which extending from the ankles to the upper torso. This suit is inflatable in various sections of the body to provide pressure to working muscles during physical activities. Use of the full body suit during physical activities has been observed to aid in the preservation of muscle tone while one is expending fat cells, resulting in a reduction of flab or excess skin.

The present invention provides a system and method for advancing healing to an abdominal incision at a faster than normal rate. The system helps to reduce pain, while permitting the patient to engage in normal, though restricted, activities that put stress on the abdominal muscles. By securing the sutured area, the invention enhances healing and prevents accidental tearing caused by coughing, laughing and sneezing, among other activities. The system further allows the patient to participate in breathing exercises and walk sooner than would normally be possible.

Figure 7:
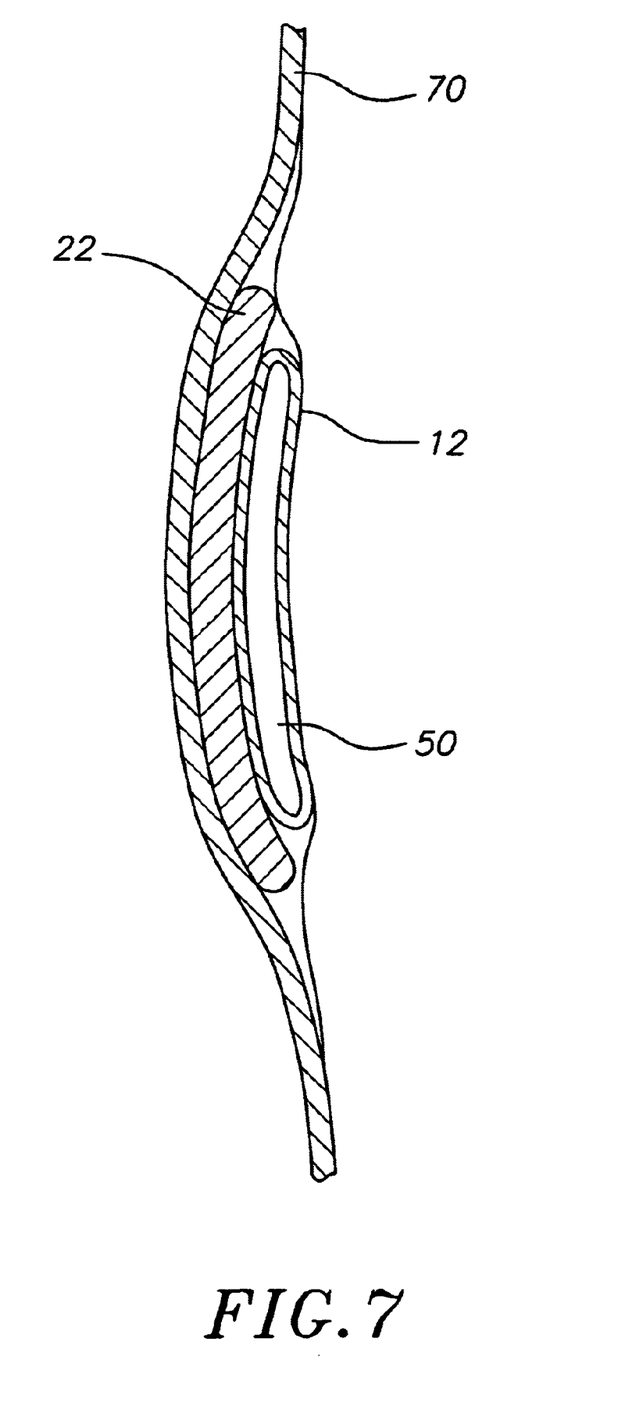
FIG. 7 is a fragmentary cross-sectional view of an alternative embodiment of the abdominal support mechanism in support of the frontal abdominal area in accordance with the invention.
Figure 8:
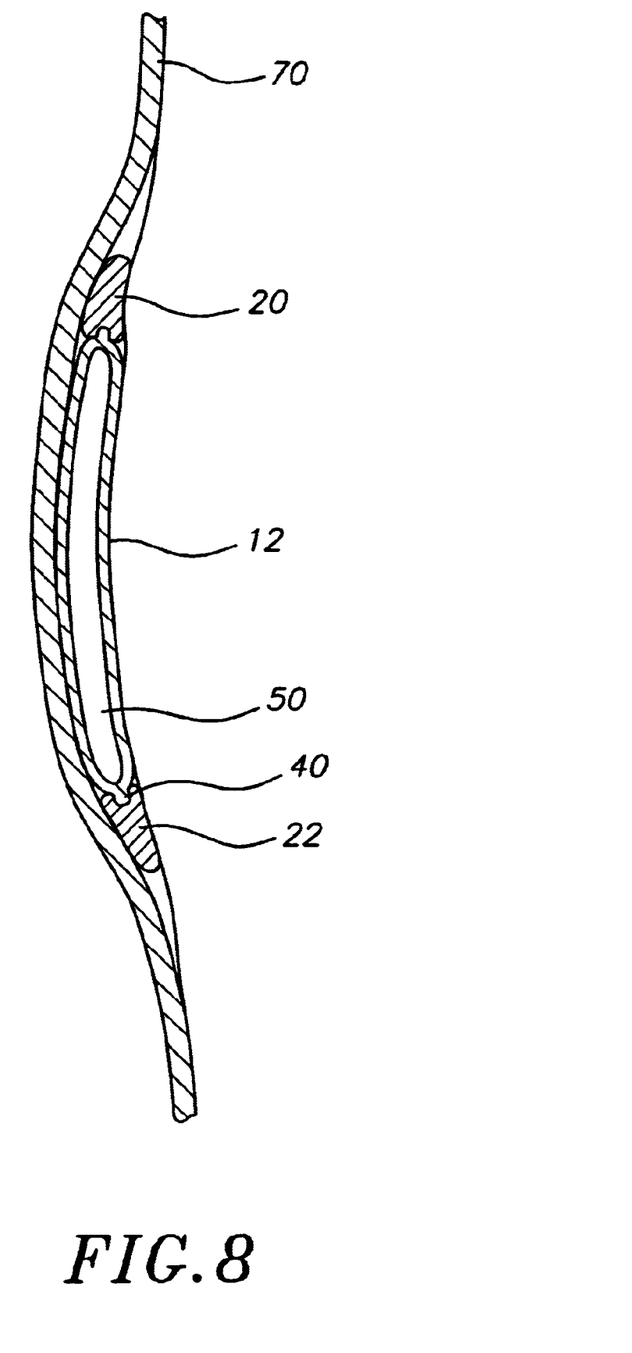
FIG. 8 is fragmentary cross-sectional view of a second alternative embodiment of the abdominal support mechanism in support of the frontal abdominal area in accordance with the invention.

While the description above has set forth a preferred embodiment of the invention, alternative embodiments may be prescribed to achieve the same benefits. One of such embodiments, as shown in FIG. 7, includes a separable inflatable bladder 50 and waist band 22, where the bladder 50 is placed against the suture and the waist band 22 is wrapped around the bladder 50 to hold it in place. FIG. 8 presents a further embodiment, which includes an inflatable bladder 50 integrated into a cutout 40 within the waist band 22, allowing the bladder 50 to expand in opposite directions.

Figure 9:
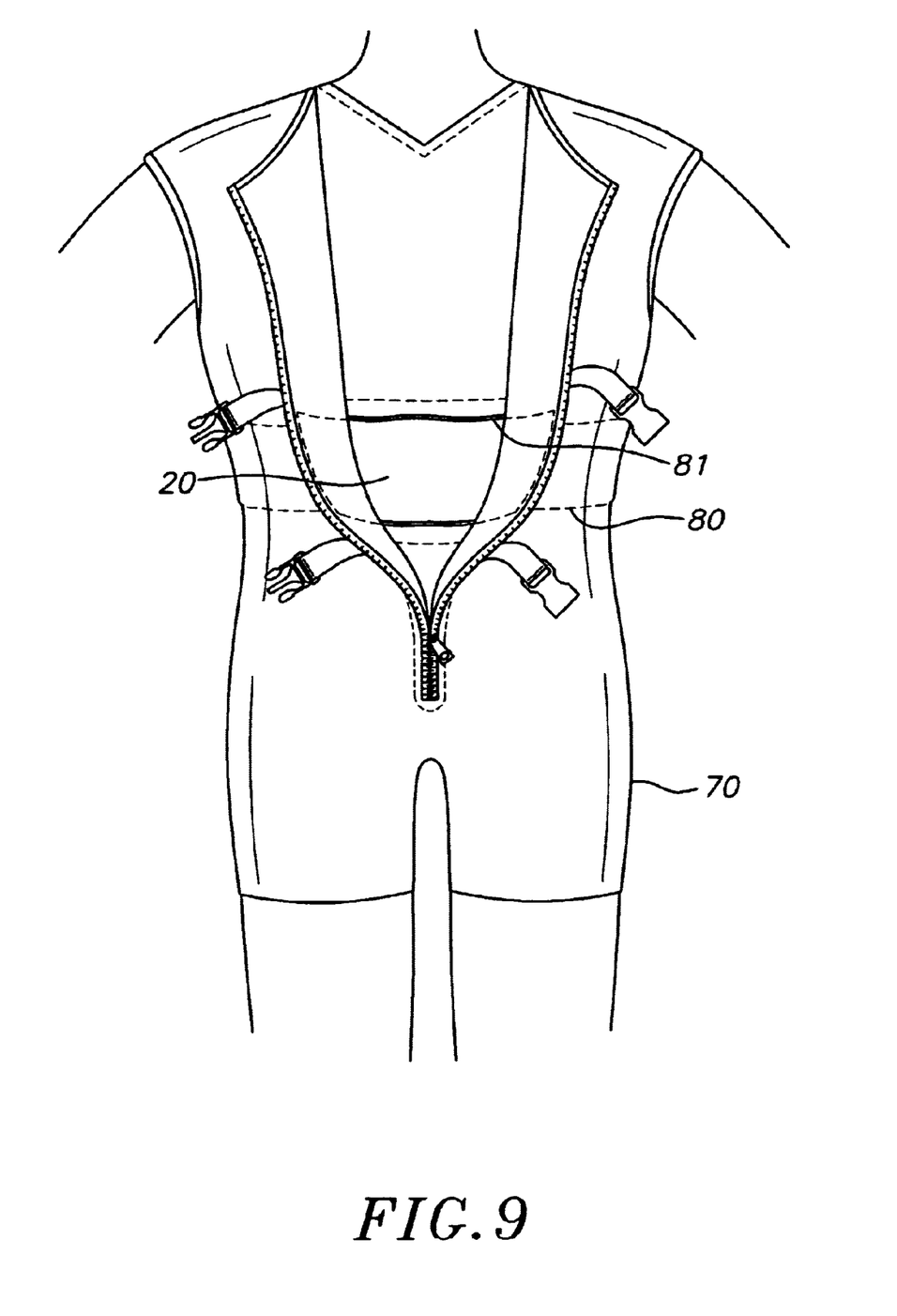
FIG. 9 is a rear view of a third alternative embodiment of the abdominal support mechanism in accordance with the invention.
Figure 10:
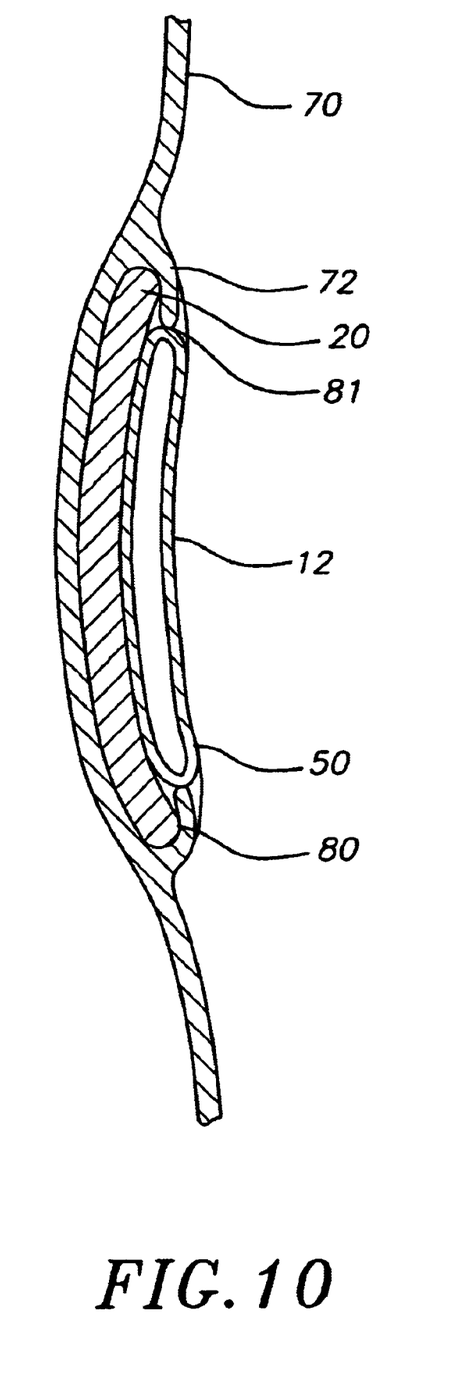
FIG. 10 is a fragmentary cross-sectional view of the alternative embodiment of the abdominal support mechanism in FIG. 8 in support of the frontal abdominal area in accordance with the invention.

FIGS. 9 and 10 describe a further alternative embodiment in which the waist band 20 and the bladder 50 are integral with the compression suit 70. The waist band 20 and bladder 50 are housed within a pocket 80 circumferentially stitched into the suit 70 in the area surrounding the waist having an opening 81 to allow the bladder 50 to expand beyond the inner liner 72.

It is to be understood that even though numerous characteristics and advantages of various embodiments of the present invention have been set forth in the foregoing description, together with details of the structure and function of various embodiments of the invention, this disclosure is illustrative only and changes may be made in detail, especially in matters of structure and arrangement of elements within the principles of the present invention to the full extent indicated by the broad general meaning of the terms in which the appended claims are expressed. For example, although the preferred embodiment described herein is directed to providing support and healing to abdominal incisions, the invention may be applied to provide support and healing to incision in the upper torso. Thus, it will be appreciated by those skilled in the art that the teachings of the present invention can be applied to other systems without departing from the scope and spirit of the present invention.

I claim:

1. A mechanism for supporting an abdominal region having an incision, the mechanism comprising a fluid impermeable expandable bladder comprising an inner wall and an outer wall, the bladder having surface areas adapted to span a portion of the abdominal region, with the inner wall contacting the incision zone and a proximal zone about it, wherein the bladder is expandable towards and conforms with the contour of the abdomen for applying pressure to the abdominal region at the incision zone and in the zone proximal to it; means for inflating the bladder with pressurizing compressible fluid to a selected pressure level; and an adjustable waistband, of an inelastic material but pliant material, encircling the waist of the user, the waistband having an inner surface and a cutouts portions within the waistband to allow the expandable bladder to expand in opposite directions, wherein a frontal area of the inner surface overlies at least a peripheral portion of the expandable bladder, and holds the bladder in juxtaposition to the abdominal region.

2. An abdominal support mechanism as set forth in claim 1, wherein the combination of the expandable bladder and the adjustable waist band provide a radial circumferential force sufficient to force facing walls of the incision together, facilitating the healing process and further, reducing pain and irritation.

3. An abdominal support mechanism as set forth in claim 2, wherein a body garment is fitted over the adjustable waistband and bladder, pressurizing all areas contiguous with the waist band upon inflation of the bladder.

4. An abdominal support mechanism as set forth in claim 3, wherein the body garment comprises a nylon-neoprene material.

5. An abdominal support mechanism as set forth in claim 2, wherein the expandable bladder exerts localized pressure forces on the abdominal area, which act to restrain the tissues in areas immediately encompassing the incision from lateral movement relative to the incision.

6. An abdominal support mechanism as set forth in claim 5, wherein the bladder and the waist band are integrally coupled to the body garment, disposed within a circumferentially stitched pocket within an inner liner of the body garment, proximal to user's waist.

7. An abdominal support mechanism as set forth in claim 1, wherein the bladder comprises a nylon coated with polyurethane material.

8. An abdominal support mechanism as set forth in claim 1, wherein the means for inflating the bladder is a hand pump further comprising a pressure relief valve.

9. An abdominal support mechanism as set forth in claim 1, wherein the waistband comprises a tightly woven fabric.

10. An abdominal support mechanism as set forth in claim 9, wherein the means for adjustably tightening the waist band comprises a belt-buckle fastener.

11. An abdominal support mechanism as set forth in claim 1, wherein the outer wall of the bladder is integrally coupled to the inner surface of the waist band inner wall along a seam.

12. An abdominal support mechanism as set forth in claim 1, wherein the waistband comprises an aperture to which the bladder is integrally coupled, and wherein the bladder expands towards as well as away from the incision zone.

13. A method of supporting the abdominal region to protect an incision therein while alleviating discomfort, comprising the steps of:
applying a fluid pressure directly to the incision zone and a proximal zone about it to a level which yields to body movement, but exerts a force which is compliant against the abdominal region, wherein the fluid pressure establishes an air pressurizing force; and providing confinement about the area generating the fluid pressure, wherein the confinement generates encircling forces on the abdominal and upper thigh regions of the body.

14. The method as set forth in claim 13, wherein the body is confined by the air pressurizing force and encircling forces, and after a period of healing, the applied forces on the body are restricted to encircling forces.

15. The method as set forth in claim 14, wherein the air pressurizing force act to force facing walls of the incision together during the healing process of the incision.

16. The method as set forth in claim 15, wherein the encircling forces act to restrain the tissues in areas immediately encompassing the incision from lateral movement relative to the incision.

17. A method of supporting an abdominal region to protect an incision therein while alleviating discomfort, comprising the steps of:
applying pressure with a compressible fluid at and about a proximal area adjacent to the incision;
applying circumferential tension about the body, wherein the circumferential tension also supports the pressure at the proximal area;
confining the trunk and abdominal area with secondary elastic pressurizing forces; and
maintaining the combination of pressurizing forces in position until initial healing has taken place and has proceeded to a desired extent.

18. The method as set forth in claim 17, wherein at least the elastic pressurizing forces are maintained on the body until the danger of rupture or separation to the incision has been minimized.

19. A method of supporting an abdominal region to protect an incision therein while alleviating discomfort, comprising the steps of:
pressurizing the surface of the abdominal region with a compressible pressurized medium which exerts localized forces that act to force facing walls of the incision together during the healing process of the incision;
supporting the pressurizing medium in juxtaposition to the abdominal region by circumferential retention about the waist of the person;
applying a secondary overlying force on the abdominal region by encompassing the trunk of the body with encircling forces acting in areas immediately encompassing the incision to restrain body tissues from lateral movement relative to the incision;
confining the trunk and abdominal regions of the body initially, with the combination of forces until initial healing has taken place and has proceeded to a desired extent; and
confining the trunk and abdominal regions of the body, after a period of healing, primarily by secondary forces until the danger of rupture or separation of the incision has been minimized.

20. A garment in combination with a mechanism for supporting an abdominal region having an incision, the mechanism comprising a fluid impermeable expandable bladder comprising an inner wall and an outer wall, the bladder having surface areas adapted to span a portion of the abdominal region, with the inner wall contacting the incision zone and a proximal zone about it, wherein the bladder is expandable towards and conforms with the contour of the abdomen for applying pressure to the abdominal region at the incision zone and in the zone proximal to it, means for inflating the bladder with pressurizing compressible fluid to a selected pressure level; and an adjustable waistband, of an inelastic, but pliable material, encircling the waist of the user, the waistband is housed within a housing means that is located in the garment, said waistband is adapted to encircle the waist of the user, said waistband having an inner surface, wherein a frontal area of the inner surface overlies at a peripheral portion of the expandable bladder, and holds the bladder in juxtaposition to the abdominal region.

21. A mechanism for supporting an abdominal region having an incision, in combination with a garment, comprising a fluid impermeable expandable bladder comprising an inner wall and an outer wall, the bladder having a surface area adapted to span a portion of the abdominal region, with the inner wall contacting the incision zone and proximal zone about it, wherein the bladder is expandable towards and conforms with the contour of the abdomen for applying pressure to the abdominal region at the incision zone and in the zone proximal to it; means for inflating the bladder with pressurizing compressible fluid to a selected pressure level; and an adjustable waistband, of an inelastic but pliable material, the waistband is located within a housing means that is located in the garment, said wasitband is adapted to encircle the waist of the user, the waistband having an inner surface, wherein a frontal area of the inner surface overlies at least a peripheral portion of the expandable bladder, and holds the bladder in juxtaposition to the abdominal region.

* * * * *